(12) United States Patent
Mehanian et al.

(10) Patent No.: US 7,397,553 B1
(45) Date of Patent: Jul. 8, 2008

(54) SURFACE SCANNING

(75) Inventors: Courosh Mehanian, Mountain View, CA (US); Steven W. Meeks, Fremont, CA (US); Eliezer Rosengaus, Palo Alto, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 72 days.

(21) Appl. No.: 11/257,234

(22) Filed: Oct. 24, 2005

(51) Int. Cl.
*G01N 21/00* (2006.01)
*G01J 4/00* (2006.01)

(52) U.S. Cl. .................... 356/237.2; 356/369

(58) Field of Classification Search ... 356/237.1–237.5, 356/239.8, 369; 250/559.41, 559.14
See application file for complete search history.

(56) References Cited

U.S. PATENT DOCUMENTS

| | | | |
|---|---|---|---|
| 4,585,348 A | 4/1986 | Chastang | |
| 4,794,264 A | 12/1988 | Quackenbos et al. | |
| 4,870,631 A | 9/1989 | Stoddard | |
| 4,873,430 A | 10/1989 | Juliana | |
| 4,905,311 A | 2/1990 | Hino et al. | |
| 5,004,929 A | * 4/1991 | Kakinoki et al. | 250/559.06 |
| 5,017,012 A | 5/1991 | Merritt, Jr. et al. | |
| 5,067,817 A | 11/1991 | Glenn | |
| 5,125,741 A | * 6/1992 | Okada et al. | 356/237.2 |
| 5,189,481 A | 2/1993 | Jann | |
| 5,270,794 A | 12/1993 | Tsuji | |
| 5,392,116 A | 2/1995 | Makosh | |
| 5,416,594 A | 5/1995 | Gross | |
| 5,604,585 A | 2/1997 | Johnson et al. | |
| 5,608,527 A | 3/1997 | Valliant et al. | |
| 5,610,897 A | 3/1997 | Yamamoto | |
| 5,633,747 A | 5/1997 | Nikoonahad | |
| 5,644,562 A | 7/1997 | de Groot | |
| 5,737,085 A | 4/1998 | Zollars et al. | |
| 5,798,829 A | 8/1998 | Vaez-Iravani | |
| 5,864,394 A | 1/1999 | Jordan | |
| 5,880,838 A | 3/1999 | Marx | |
| 5,883,714 A | 3/1999 | Jann et al. | |
| 5,898,500 A | 4/1999 | Canteloup et al. | |
| 5,903,342 A | 5/1999 | Yatsugake | |
| 5,963,314 A | 10/1999 | Worster et al. | |
| 5,985,680 A | 11/1999 | Singhal | |
| 5,986,763 A | 11/1999 | Inoue | |
| 5,995,226 A | 11/1999 | Abe | |
| 6,020,966 A | 2/2000 | Ausschnitt et al. | |
| 6,031,615 A | 2/2000 | Meeks | |
| 6,081,325 A | 6/2000 | Leslie | |
| 6,091,493 A | 7/2000 | Stover et al. | |
| 6,122,046 A | 9/2000 | Almogy | |
| 6,130,749 A | 10/2000 | Meeks | |
| 6,154,280 A | 11/2000 | Borden | |
| 6,169,601 B1 | 1/2001 | Eremin et al. | |

(Continued)

FOREIGN PATENT DOCUMENTS

DE   4105192   8/1991

(Continued)

*Primary Examiner*—Hoa Q Pham
(74) *Attorney, Agent, or Firm*—Caven & Aghevli LLC

(57) ABSTRACT

In one embodiment, a surface scanning system comprises a radiation directing assembly that scans a surface using a Cartesian scanning pattern; and a radiation collecting assembly that collects radiation reflected from the surface. A scattered radiation collection system is included that measures the scattered light from the surface.

15 Claims, 13 Drawing Sheets

U.S. PATENT DOCUMENTS

| | | | |
|---|---|---|---|
| 6,172,752 B1 | 1/2001 | Haruna et al. | |
| 6,198,533 B1 | 3/2001 | Meeks | |
| 6,229,610 B1 | 5/2001 | Meeks | |
| 6,268,919 B1 | 7/2001 | Meeks | |
| 6,392,749 B1 | 5/2002 | Meeks | |
| 6,433,877 B2 | 8/2002 | Watanabe et al. | |
| 6,449,036 B1 * | 9/2002 | Wollmann et al. | 356/237.2 |
| 6,515,745 B2 | 2/2003 | Vurens et al. | |
| 6,556,290 B2 | 4/2003 | Maeda et al. | |
| 6,617,603 B2 | 9/2003 | Ishiguro et al. | |
| 6,624,884 B1 | 9/2003 | Imaino | |
| 6,624,894 B2 | 9/2003 | Olszak et al. | |
| 6,665,078 B1 | 12/2003 | Meeks | |
| 6,678,046 B2 | 1/2004 | Opsal | |
| 6,687,008 B1 | 2/2004 | Peale et al. | |
| 6,690,473 B1 | 2/2004 | Stanke et al. | |
| 6,704,435 B1 | 3/2004 | Imaino | |
| 6,717,671 B1 | 4/2004 | Meeks | |
| 6,751,044 B1 | 6/2004 | Meeks | |
| 6,757,056 B1 | 6/2004 | Meeks | |
| 6,781,103 B1 | 8/2004 | Lane | |
| 6,804,003 B1 | 10/2004 | Wang et al. | |
| 6,813,034 B2 | 11/2004 | Rosencwaig et al. | |
| 6,909,500 B2 * | 6/2005 | Meeks | 356/237.3 |
| 6,917,433 B2 | 7/2005 | Levy et al. | |
| 6,940,609 B2 | 9/2005 | Scheiner | |
| 6,956,660 B2 | 10/2005 | Meeks et al. | |
| 7,019,850 B2 | 3/2006 | Finarov | |
| 7,023,547 B2 | 4/2006 | Venkatasubbarao et al. | |
| 7,042,556 B1 | 5/2006 | Sun | |
| 7,042,577 B1 | 5/2006 | Jacob et al. | |
| 7,046,352 B1 | 5/2006 | Dayal et al. | |
| 7,075,630 B2 | 7/2006 | Meeks | |
| 7,113,284 B1 | 9/2006 | Meeks | |
| 7,161,668 B2 * | 1/2007 | Meeks et al. | 356/237.2 |
| 7,161,683 B2 | 1/2007 | Weitzel | |
| 7,218,391 B2 * | 5/2007 | Meeks | 356/237.2 |
| 2002/0015146 A1 | 2/2002 | Meeks | |
| 2002/0107650 A1 | 8/2002 | Wack et al. | |
| 2002/0145740 A1 | 10/2002 | Meeks | |
| 2002/0163634 A1 | 11/2002 | Meeks | |
| 2003/0025905 A1 | 2/2003 | Meeks | |
| 2003/0179370 A1 | 9/2003 | Goldberg et al. | |
| 2004/0017561 A1 | 1/2004 | Meeks | |
| 2004/0046959 A1 | 3/2004 | Meeks | |
| 2004/0130710 A1 | 7/2004 | Hwang et al. | |
| 2004/0160604 A1 | 8/2004 | Meeks | |
| 2004/0169850 A1 | 9/2004 | Meeks | |
| 2004/0233419 A1 | 11/2004 | Meeks | |
| 2005/0057747 A1 | 3/2005 | Meeks | |
| 2005/0206888 A1 | 9/2005 | Yoshida et al. | |
| 2006/0072106 A1 | 4/2006 | Matsui et al. | |
| 2007/0030493 A1 | 2/2007 | Zettler et al. | |

FOREIGN PATENT DOCUMENTS

| | | |
|---|---|---|
| EP | 080540 | 6/1983 |
| JP | 03085514 | 4/1991 |
| JP | 07055702 | 3/1995 |
| JP | 10325711 | 12/1998 |
| WO | WO 9416319 | 7/1994 |

* cited by examiner

SURFACE SCANNING

BACKGROUND

The subject matter described herein relates to surface inspection techniques, and more particularly to surface scanning, for materials such as, for example, semiconductor materials.

When a patterned wafer is illuminated, the intensity of scattered and reflected light is dependent on the orientation of the incoming radiation with respect to the pattern. Thus, a spiral scan of a patterned wafer will have variations in image intensity as a function of azimuthal angle (as measured from the center of the wafer). The intensity variations complicate the algorithms required to extricate defect information from the image and can dramatically reduce the sensitivity to a variety of defect types. Other modes of surface scanning may be useful for reducing these artifacts.

BRIEF DESCRIPTION OF THE DRAWINGS

The detailed description is described with reference to the accompanying figures.

SUMMARY

In one embodiment, a surface scanning system comprises a radiation directing assembly that scans a surface using a Cartesian scanning pattern; and a radiation collecting assembly that collects radiation reflected from the surface. A scattered radiation collection system is included that measures the scattered light from the surface.

DETAILED DESCRIPTION

Described herein are multiple embodiments of systems and methods for surface scanning. In the following description, numerous specific details are set forth in order to provide a thorough understanding of various embodiments. However, it will be understood by those skilled in the art that the various embodiments may be practiced without the specific details. In other instances, well-known methods, procedures, components, and circuits have not been described in detail so as not to obscure the particular embodiments.

Various methods described herein may be embodied as logic instructions on a computer-readable medium. When executed on a processor the logic instructions cause a processor to be programmed as a special-purpose machine that implements the described methods. The processor, when configured by the logic instructions to execute the methods described herein, constitutes structure for performing the described methods.

Embodiments of a surface scanning device described herein collect multiple channels of information, including specular and scatter data, as well as the phase shift induced in the specular beam by the reflecting medium. Various optical testing components and techniques for surface inspection are described in U.S. Pat. Nos. 6,665,078, 6,717,671, and 6,757,056, and 6,909,500 to Meeks, et al., the disclosures of which are incorporated herein by reference in their entirety.

Embodiments described herein may perform film thickness measurements, surface roughness measurement, reflectivity measurement, magnetic imaging, and optical profiling using radiation in the optical spectrum. In alternate embodiments radiation outside the optical spectrum may be used.

Figure 1:
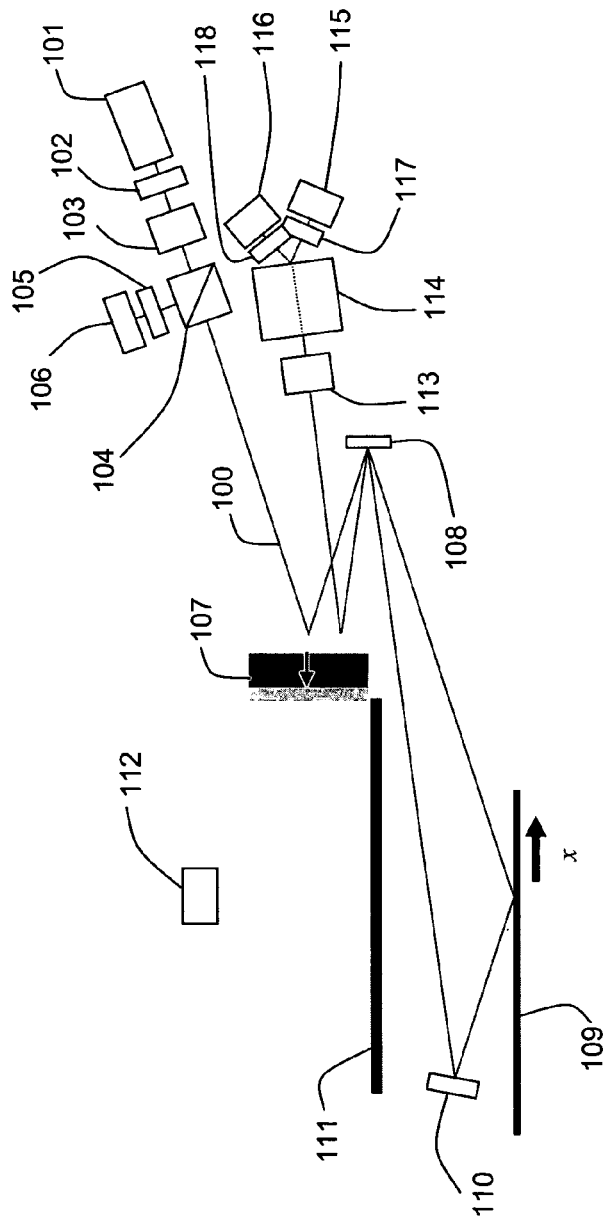
FIG. 1 is a side view of a first embodiment of a system for surface scanning.
Figure 2:
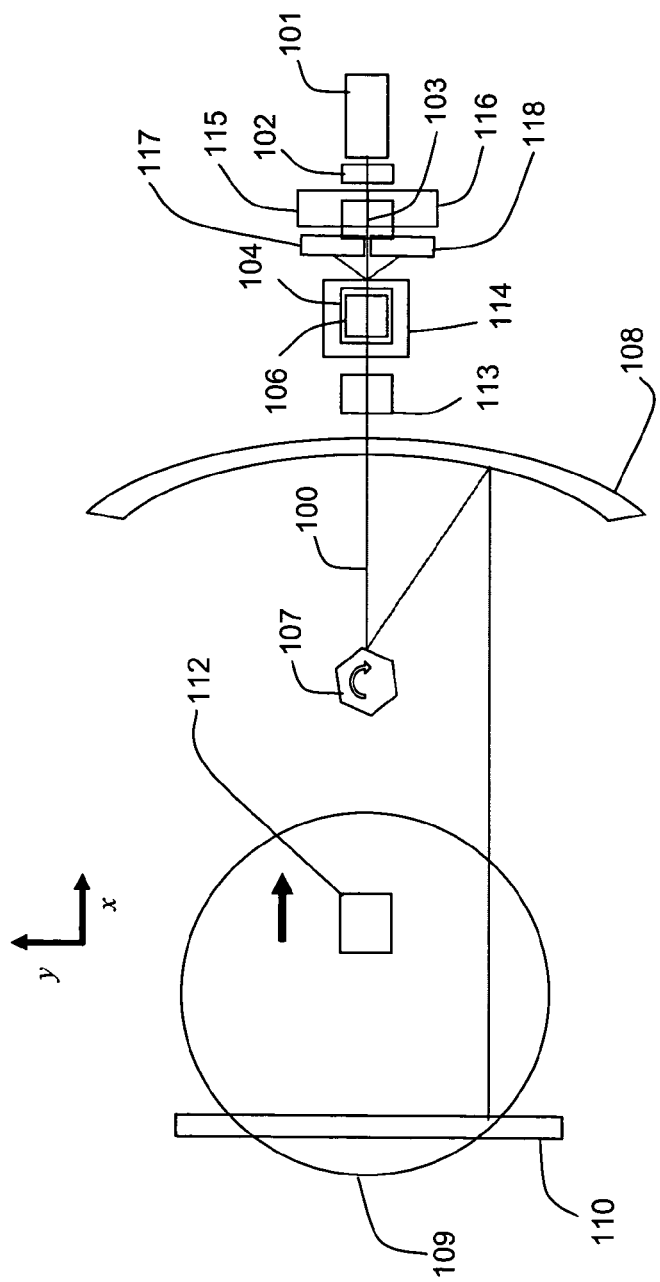
FIG. 2 is a top view of a first embodiment of a system for surface scanning.
Figure 3:
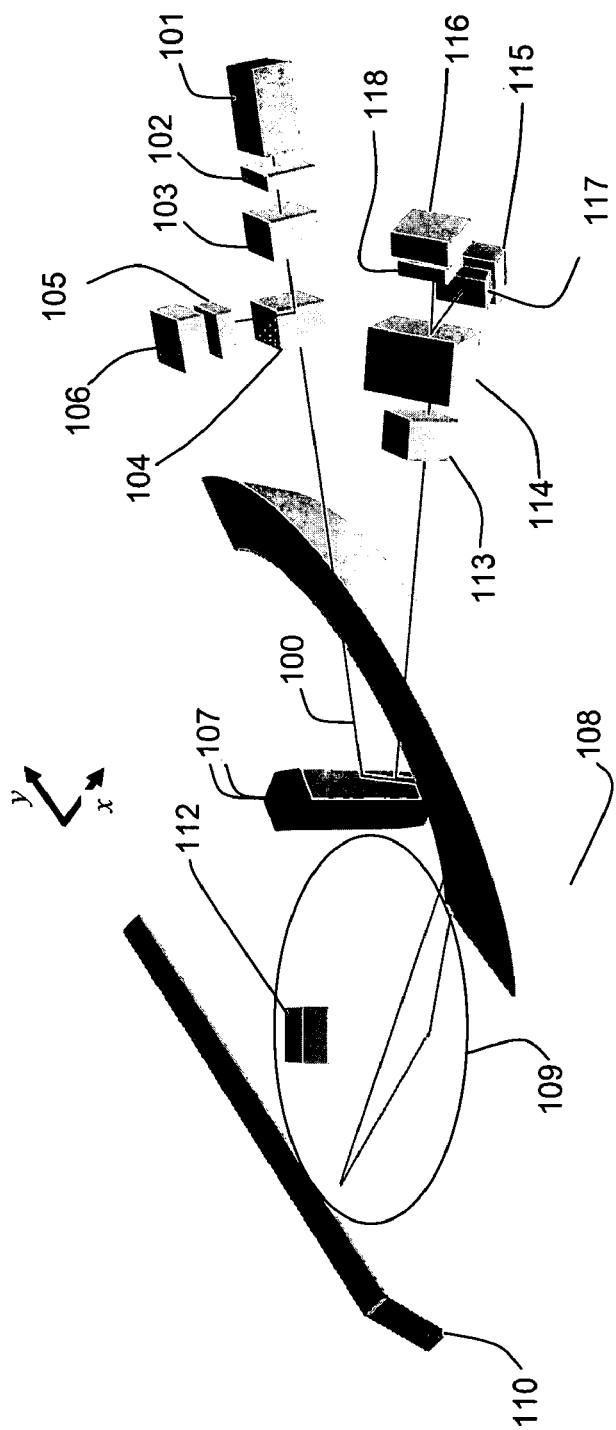
FIG. 3 is a perspective view of a first embodiment of a system for surface scanning.

A first embodiment of a system for surface scanning is presented in FIGS. 1-3. FIG. 1 is a side view of an embodiment of a system for surface scanning, and FIGS. 2 and 3 are top and perspective views, respectively, of the system depicted in FIG. 1. Referring to FIGS. 1-3, the surface scanning system includes a laser 101. In one embodiment, laser 101 may be embodied as a multi-mode, multi-wavelength laser diode that is commercially available from Rohm Co., LIE Kyoto, Japan as model number RLD-78MV, and produces a laser beam 100. Alternative lasers are an 8 mw, 635 nm ULN laser diode available from Coherent.

The scanning system may further include a polarizer 102 which may be adjusted for P polarization and which improves the extinction ratio of the laser 101. A mechanically rotatable half wave plate 103 such as are commercially available from CVI Laser Corp. may be used to rotate the polarization between 45 degrees, and P or S polarizations. In alternate embodiments, the laser 101 may be rotated in order to rotate the polarization. In alternate embodiments, a liquid crystal polarization rotator such as model LPR-100 available from Meadowlark Optics, Frederick, Colo. may be used to rotate the polarization. The latter embodiment has the advantage of being a purely electronic means of polarization rotation and as a result there is no possibility of beam movement when the polarization is rotated.

The system may further include an optional non-polarizing beam splitter (optional) 104 to provide a reference beam to stabilize the laser intensity. The reference beam may be directed through a diffuser 105 and measured by a photodiode 106. The output from the photodiode 106 may be used to stabilize the intensity output of the laser 101. Components 101-106 direct radiation toward the surface of the wafer 109, and therefore may be considered a radiation directing assembly.

The laser beam 100 strikes a rotating mirror 107 which scans the beam across the face of a parabolic mirror 108. In one embodiment the rotating mirror 107 is shaped as a polygon in cross-section (See, FIGS. 2, 3). The mirror 108 has parabolic shape in the horizontal projection and is flat in the vertical direction. In one embodiment, the polygonal mirror 107 is positioned at the focal axis of the parabolic mirror 108 such that the horizontal projection of the beam reflected from 108 is parallel to the axial plane of the parabola.

There are a number of alternatives to the rotating polygonal scanner. For example, the rotating polygonal scanner may be replaced by a mirror galvanometer. One advantage of a mirror galvanometer over the rotating polygonal mirror is that the intersection of the incident beam and the galvanometer mirror surface remains closer to the focus of the parabola during its entire motion. Another alternative is to use a flat rotating mirror with the backside covered by an absorptive black material. The flat rotating mirror may be positioned such that the axis of rotation coincides with the reflective surface.

In one embodiment, the vertical angle of the beam is adjusted such that the beam strikes the wafer 109 at an oblique angle. The angle of incidence shown in FIG. 1 is approximately 65 degrees from an axis normal to the surface of wafer 109, but angles greater or less than 65 degrees will work. The reflected beam propagates towards a flat mirror 110 whose long axis is perpendicular to the parabola's axis. The flat mirror 110 is angled slightly vertically towards the parabolic mirror so that the reflected beam returns to approximately the same point on the parabolic mirror from whence it was originally reflected. On the return path, however, the beam is coming at a less steep angle so that when it reflects from the parabolic mirror it will strike the polygonal mirror at a lower point than where it initially struck.

After reflecting off of the polygonal mirror, the return beam passes through a mechanically rotatable quarter wave plate 113, commercially available from CVI Laser Corp. The beam is then polarization split with a Wollaston prism 114 available from CVI Laser Corp., for example, and each polarization component is detected with a separate photodetector. The plane of the Wollaston prism (the plane of the split beams) is adjusted at 45 degrees to the plane of incidence. The first mixed component of the beam (which includes both P and S components with respect to the plane of incidence) is directed to a conventional photodiode 115 available from Hamamatsu Corp., for example, and the second mixed component (which includes both P and S components with respect to the plane of incidence) is directed to a conventional photodiode 116. The photodiodes may include a diffuser 117 and 118 placed in front of them to reduce the residual position sensitivity of the photodiodes. The difference between the signals produced by the photodetectors is proportional to the cosine of the phase difference between the first and second mixed components coming from the Wollaston prism. As a result, this instrument can get different types of information when used in different modes. The diffusers 117 and 118 are optional. The photodiodes 115 and 116 may be replaced with quadrant detectors (without any diffusers). If this is done the optical system will also be capable of measuring the slope of the surface. The slope may be integrated and filtered to obtain the profile of the surface. Components 113-118 collect radiation reflected from the surface, and therefore may be considered radiation collecting assemblies.

In one embodiment, a Fresnel lens 111 is used to collect the scattered light for the purposes of detecting scattering defects on the wafer. The Fresnel lens 111 is omitted from FIGS. 2-3 to permit the underlying wafer 109 to be visible. The scattered light is measured with a photodetector 112 placed near the back focal point of the Fresnel lens. More than one Fresnel lens may be added to the scattered light detection optics. For example, a pair of Fresnel lenses can be used to segment the scattered light and improve the ability to classify defects. Alternatively, the outputs from the pair of lenses (and their detectors) may be added to improve sensitivity. One advantage of using a Fresnel lens is that it is a very low cost and can have a very large diameter.

When the incident polarization is adjusted to P (by rotating the half wave plate 103), the P specular and P scattered light is measured, resulting in sensitive measurements of defects in underlying layers. The P specular signal is given by the sum of the signals from 115 and 116. When the polarization is adjusted to S polarization ((by rotating the half wave plate 103) the instrument will he able to measure the S specular and the S scattered light and, as a result, the system will be less sensitive to underlying layers and more sensitive to defects at the topmost surface. The S specular signal is given by the sum of the signals from 115 and 116.

When the polarization is adjusted to 45 degrees (exactly between P and S polarization) the instrument is most sensitive to measurements of the phase change induced by changes in the resist profile on the wafer surface. This mode is called the phase shift mode and the incident polarization is termed Q. The phase shift is measured by taking the difference between the signals measured at 115 and 116. This gives an output that is proportional to the cosine of the phase difference between the first and second mixed components of the wave. The orientation of the quarter wave plate 113 is adjusted to optimize detection of focus and exposure errors. The individual components may also be measured; that is, the first and second mixed components of the 45 degrees polarized light. These are measured simultaneously with the phase shift and the scattered light. The first and second mixed components of the 45 degree linearly polarized light are referred to as $S_q$ and $P_q$.

Figure 4:
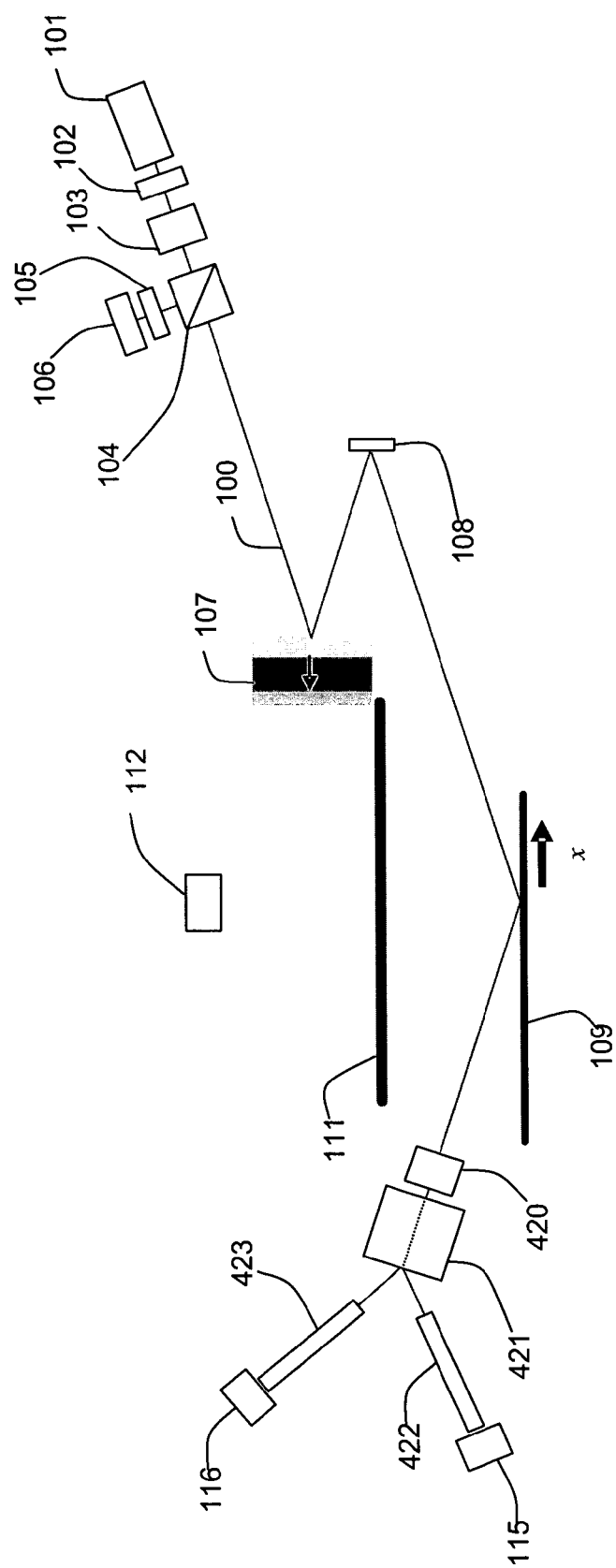
FIG. 4 is a side view of a second embodiment of a system for surface scanning.
Figure 5:
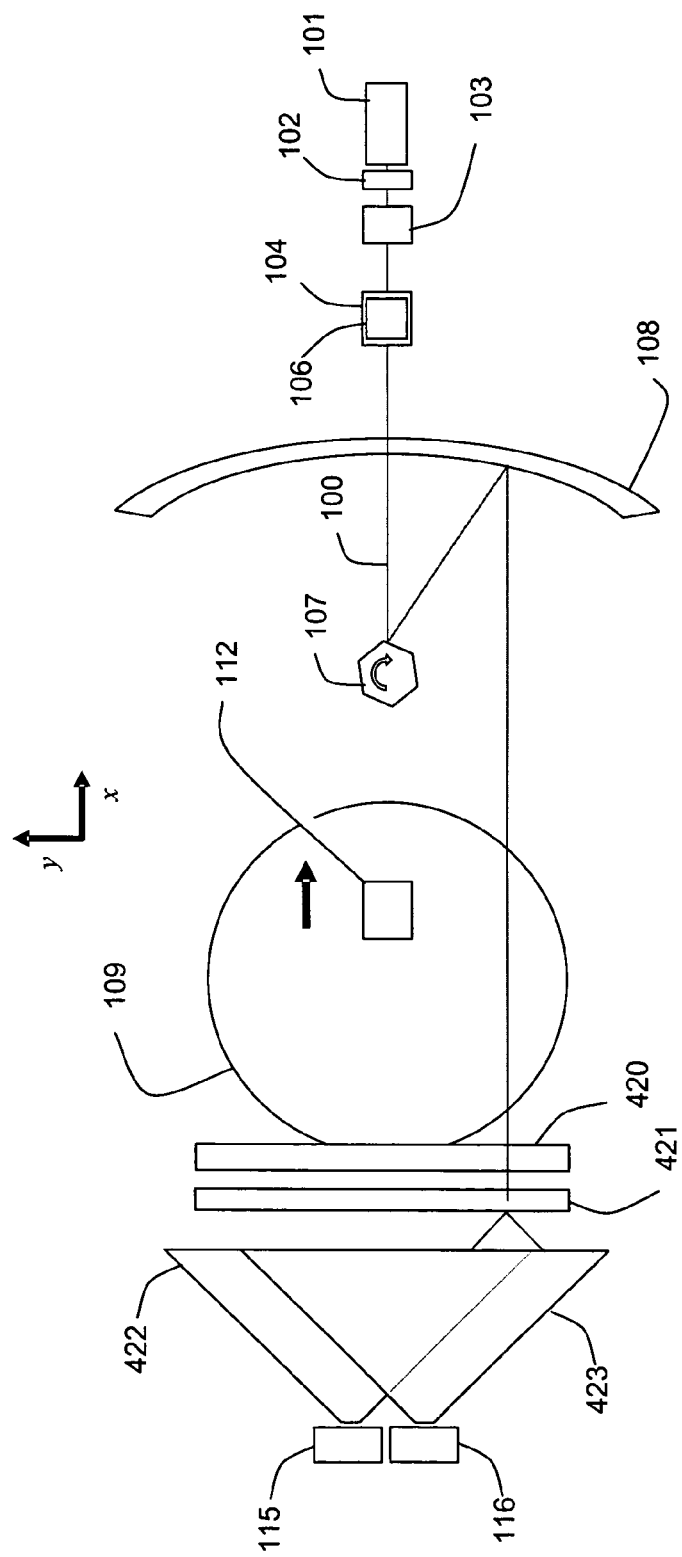
FIG. 5 is a top view of a second embodiment of a system for surface scanning.
Figure 6:
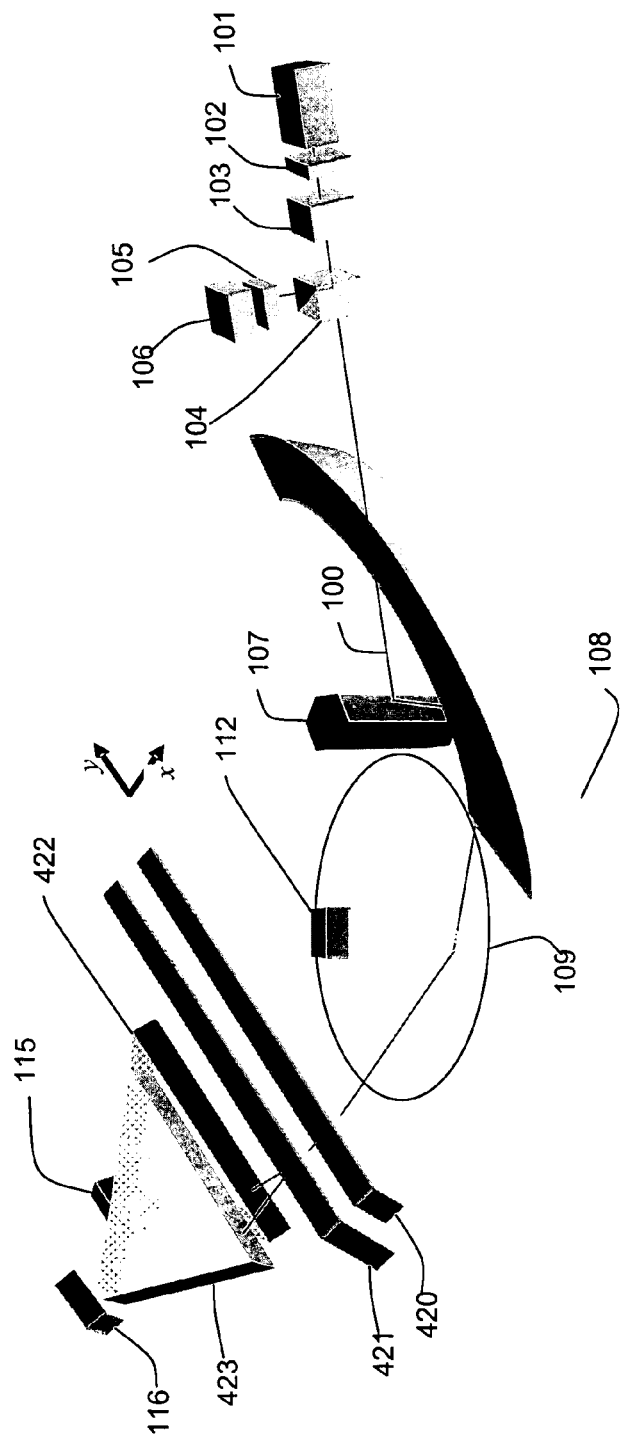
FIG. 6 is a perspective view of a second embodiment of a system for surface scanning.

FIGS. 4-6 are schematic illustrations of a second embodiment of a surface scanning system. Many of the components of the system depicted in FIGS. 4-6 are the same as those depicted in FIGS. 1-3. For clarity, these components retain the same reference numerals.

Referring to FIGS. 4-6, after the beam is reflected off of the wafer, it passes through a quarter wave plate 420, which may be embodied as a liquid crystal polarization rotator. The beam is then polarization split with a Wollaston prism 421 or other polarizing beam splitter. The plane of the Wollaston prism (the plane of the split beams) is adjusted at 45 degrees to the plane of incidence. Each split beam is detected separately using a telecentric arrangement. This can be accomplished using transparent sheets 422 and 423 (i.e. acrylic or glass) with one edge polished and coated with an anti-reflective material. Light exiting the polarizing beam splitter 421 enters the sheets 422, 423 through this edge and is confined inside the sheet by total internal reflection (TIR). The opposing edge of the sheets 422, 423 can be positioned adjacent to the face of detectors 115, 116, respectively. This can be accomplished, for example, by deforming the heated sheet into a rolled configuration at one end, while being straight at the opposite end. The rolled end can be cut and polished, and then butted to the detectors 115 and 116, typically photodiodes or PMTs.

Figure 7:
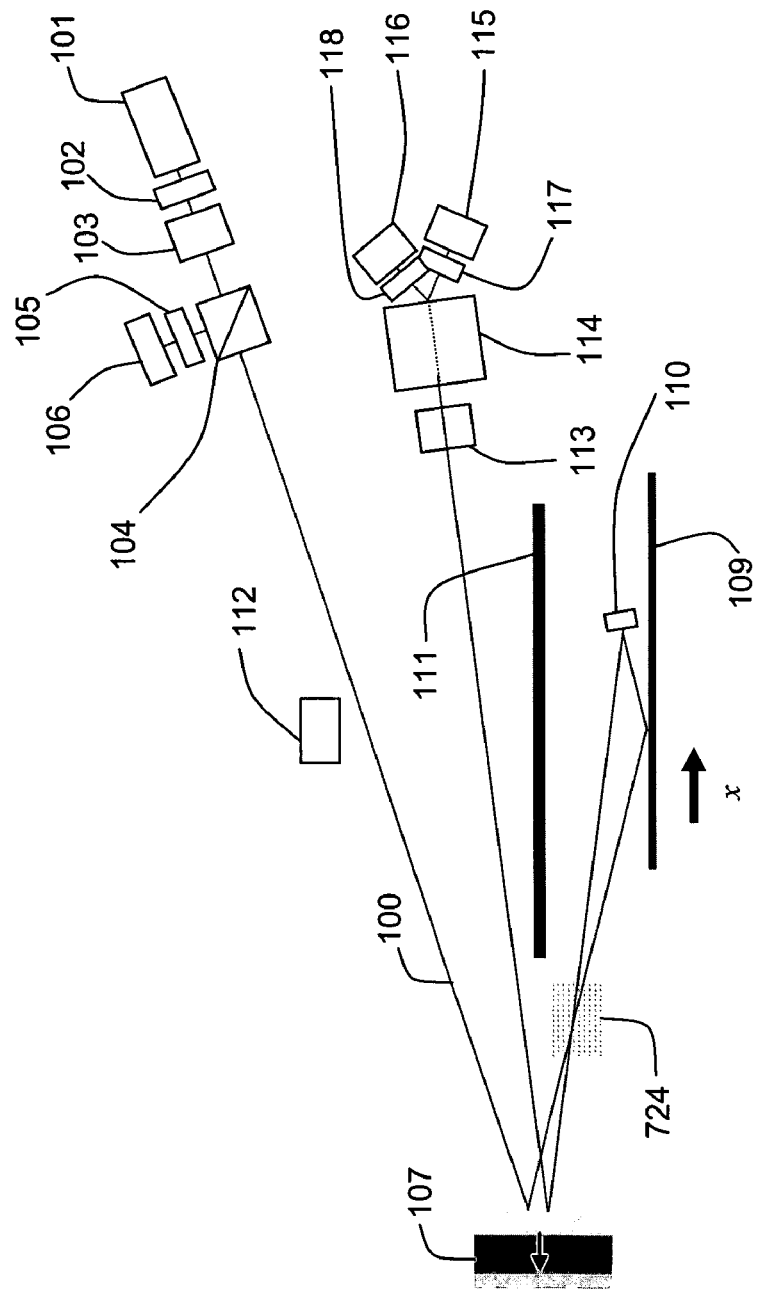
FIG. 7 is a side view of a third embodiment of a system for surface scanning.
Figure 8:
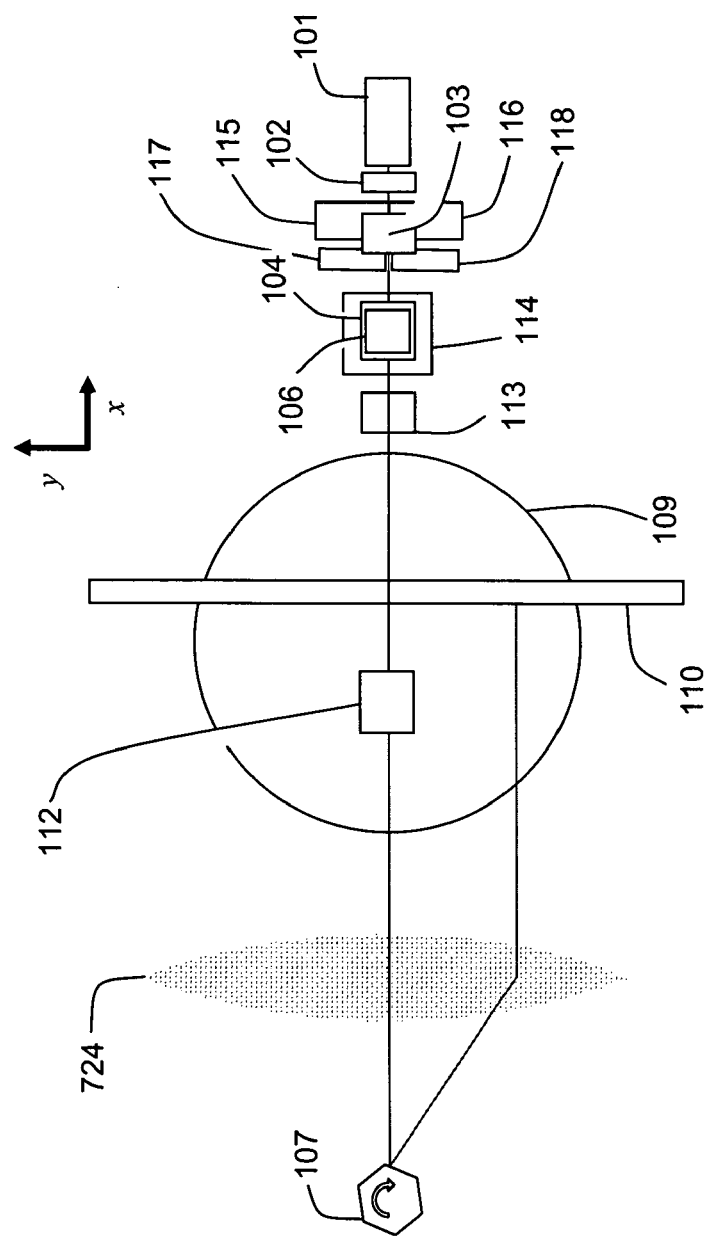
FIG. 8 is a top view of a third embodiment of a system for surface scanning.
Figure 9:
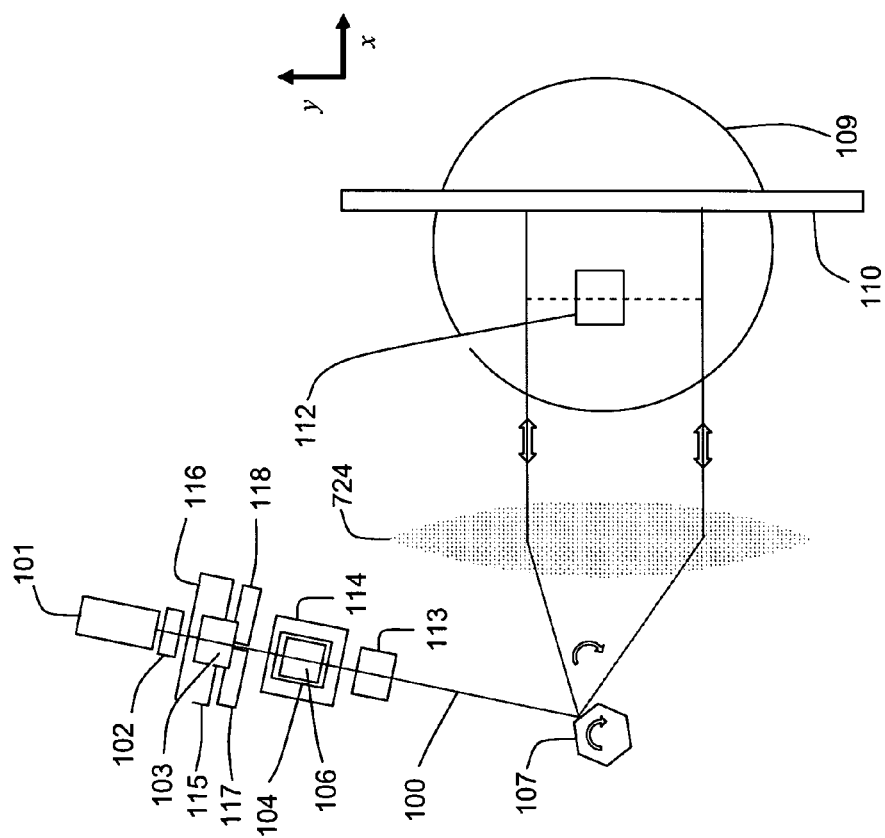
FIG. 9 is a top view of a fourth embodiment of a system for surface scanning.

FIGS. 7-9 are schematic illustrations of a third embodiment of a surface scanning system. Many of the components of the system depicted in FIGS. 7-9 are the same as those depicted in FIGS. 1-6. For clarity, these components retain the same reference numerals.

The embodiments depicted in FIGS. 7-9 use a telecentric scan lens 724 instead of a parabolic mirror to cause the beam to impinge on the wafer at a constant angle. Referring briefly to FIGS. 7-8, in one embodiment a scan lens 724 may be interposed between the mirror 107 and the wafer 109. Radiation reflected from the mirror 107 passes through the scan lens 724, which focuses the radiation onto the surface of wafer 109. Radiation reflected from the surface of wafer 109 is reflected by planar mirror 110 back through scan lens 724, which focuses the radiation back onto rotating mirror 107 to detection components 113-118.

FIG. 9 is a schematic illustration of an alternate design using a scan lens 724. The embodiment depicted in FIG. 9 is similar to the embodiment depicted in FIG. 8, but the optical components and the rotating mirror 107 are disposed on the same side of the flat mirror 110, enabling a more compact design.

One advantage of a design that incorporates a telecentric lens such as lens 724 is that it allows for a smaller spot size. The spot size may be adjusted by controlling the laser beam diameter and or the focal length of the telecentric scan lens. A 100 mm by 100 mm area may be scanned with 100% coverage by a 20 micron diameter spot in a time of 4 seconds using an octagonal polygon rotating at 12,000 rpm. The telecentric lens may be embodied as a section of a spherical lens or a complete spherical lens.

In one embodiment, the system implements a Cartesian scanning pattern, in which the width of the wafer (i.e., the y-direction) is scanned when the polygonal mirror turns through one of its facets. The wafer 109 is moved (i.e., in the x-direction) under the beam in order to scan the entire wafer. Current fabrication technology produces wafers that are 300 mm in width. This requires the use of a parabolic mirror 108 that is at least 300 mm across to scan the incident laser beam across the wafer at a constant angle and to de-scan the reflected beam to the detection system.

Figure 10:
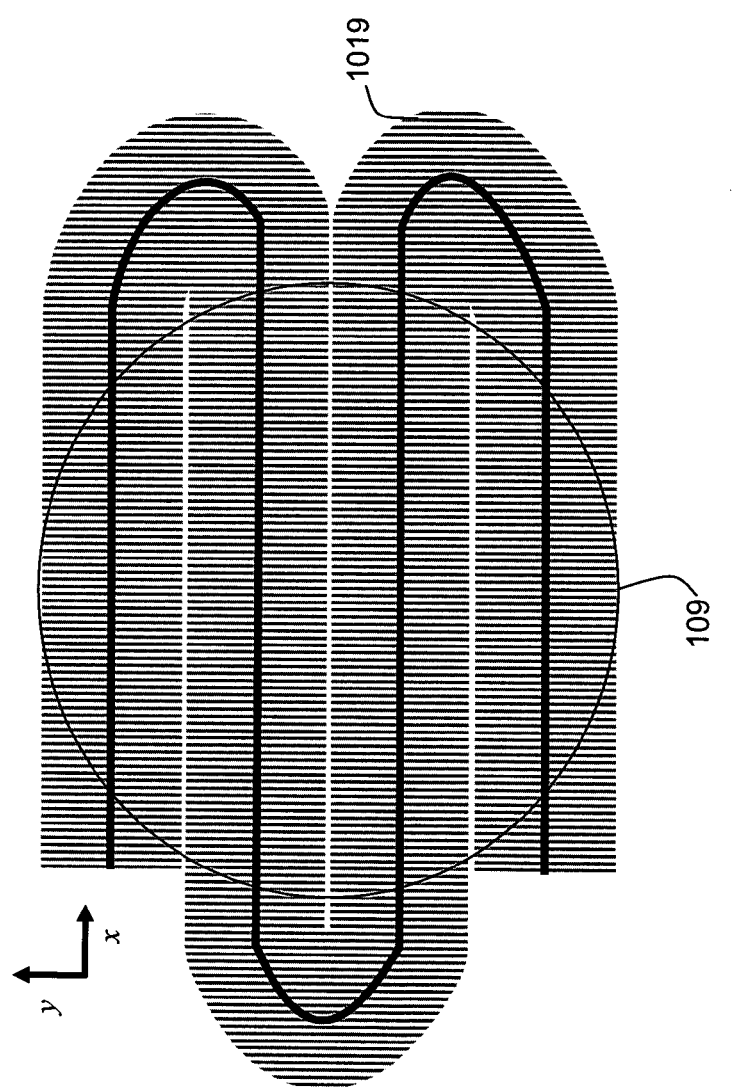
FIG. 10 is a top view of a serpentine scanning pattern.

The 300 mm width requirement places limitations on the precision of the parabolic mirror. It is possible to relax these requirements and cost by reducing the width of the scan so that only a portion of the wafer is scanned for each rotation of the polygonal mirror through one of its facets. As an example, the scan width may be reduced to one quarter of the wafer width. This allows the parabolic mirror to be made smaller and cheaper, or to use only its center portion where there is less distortion. To scan the entire wafer, the wafer may be moved in a serpentine direction 1019 such that the wafer is scanned in multiple swaths as shown in FIG. 10.

Figure 11:
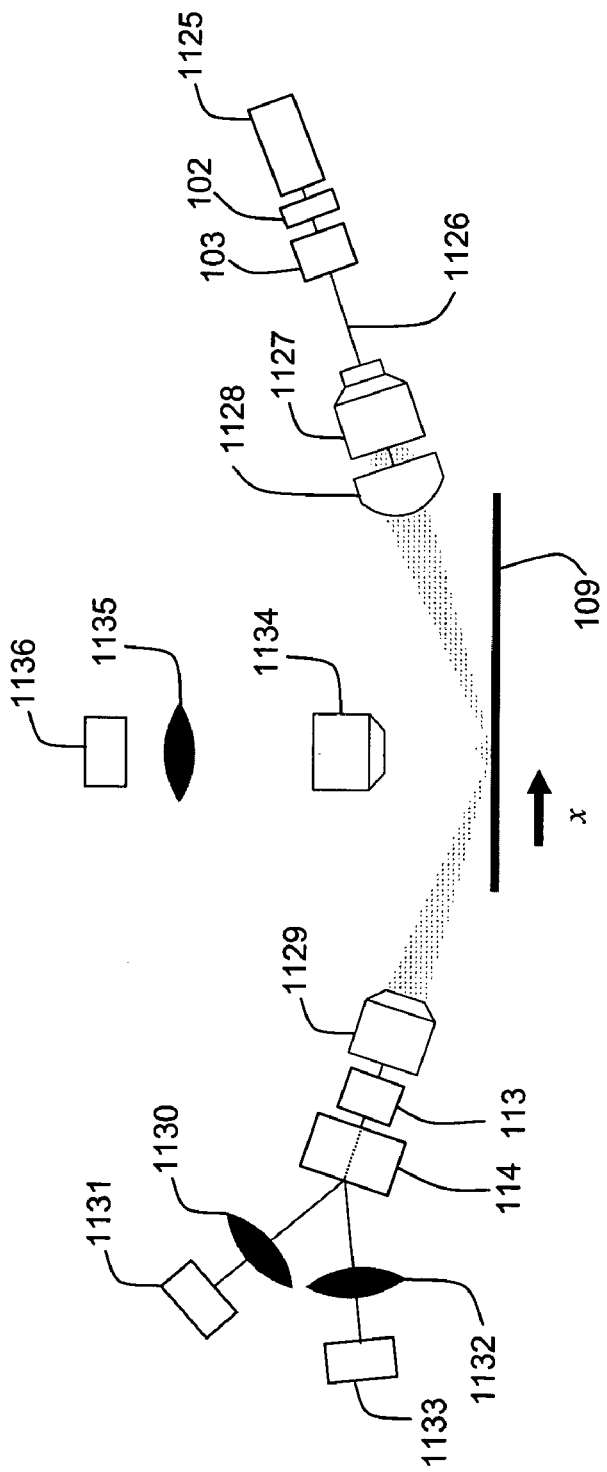
FIG. 11 is a side view of a fifth embodiment of a system for surface scanning.
Figure 12:
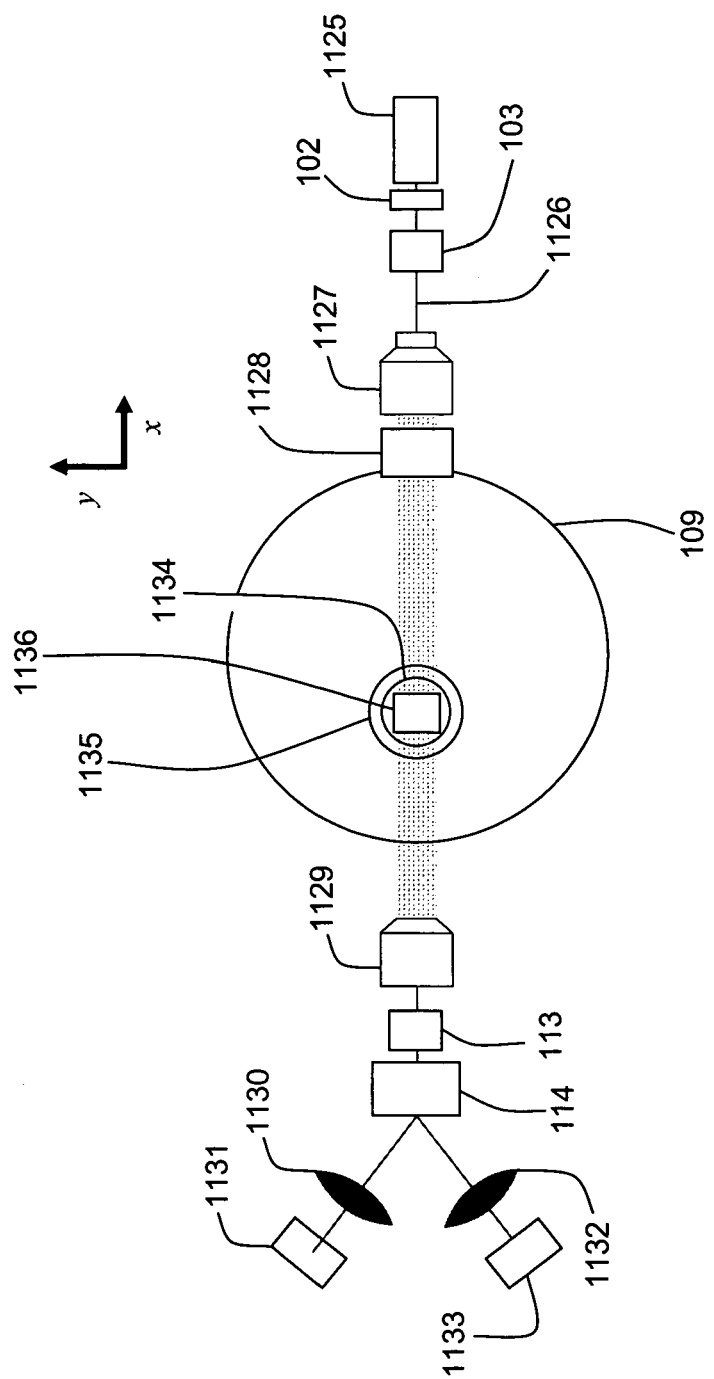
FIG. 12 is a top view of a fifth embodiment of a system for surface scanning.
Figure 13:
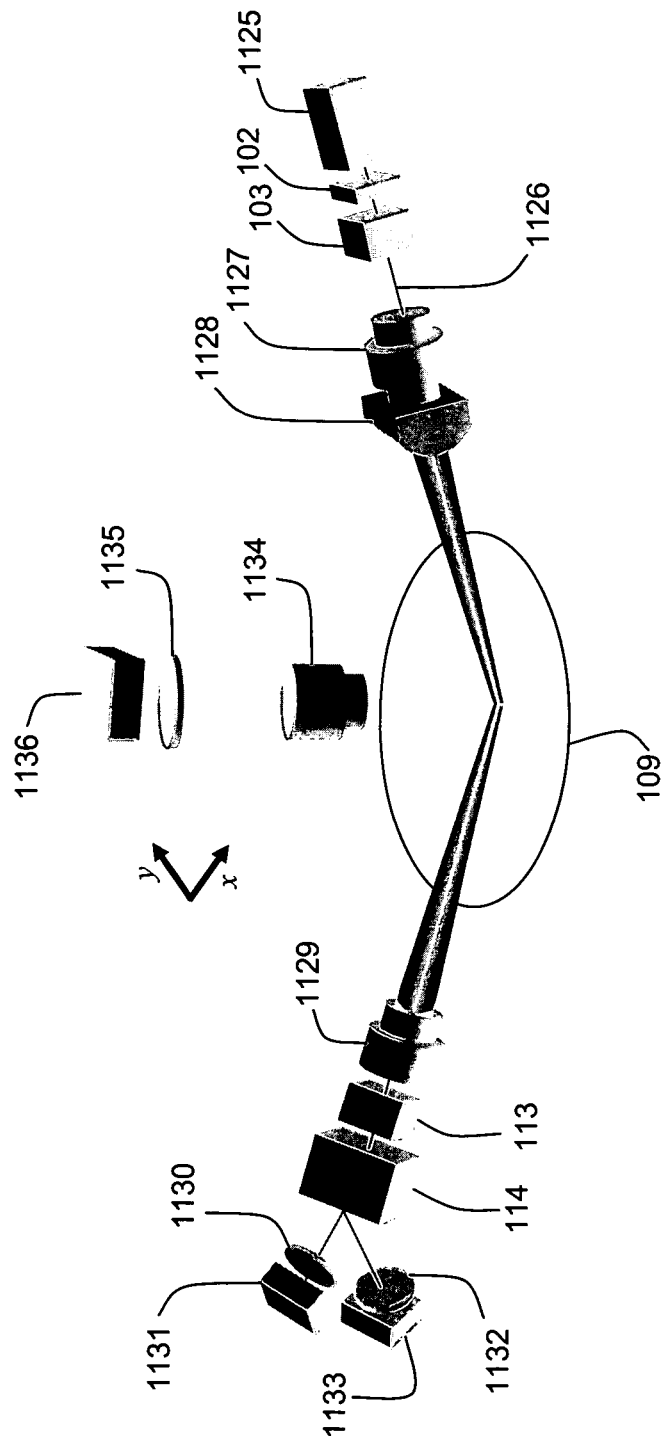
FIG. 13 is a perspective view of a fifth embodiment of a system for surface scanning.

FIGS. 11-13 are schematic depictions of an embodiment which uses an imaging technique to measure specular, scatter, and phase shift data reflected from the surface of a wafer. FIGS. 11, 12 and 13 are the side, top, and perspective views, respectively, of the imaging embodiment. The technique uses imaging in the y-direction and scanning in the x-direction. The wafer may be scanned in a serpentine path as described with reference to FIG. 10. This embodiment allows fast inspection of the entire wafer surface while illuminating and collecting telecentrically.

Referring to FIGS. 11-13, a laser 1125, such as a HeNe laser available from Coherent, produces a laser beam 1126. The laser beam is polarized by a polarizer 102 which is adjusted for P polarization. The next element is a mechanically rotatable half wave plate 103, or a liquid crystal polarization rotator, which is used to rotate the polarization to P or S polarization, or to Q, 45 degrees between them. A beam expander 1127, which is commercially available from Coherent, is used to expand the beam. The beam width corresponds to the width of the scanning swath in the y-direction. A cylindrical lens 1128 focuses the beam in the x-direction, while leaving the beam width in the y-direction unchanged.

The beam expander 1127 and cylindrical lens 1128 generate a rectangularly-shaped spot on the surface of the wafer 109 with the long direction along the y-axis. The vertical angle of the beam may be adjusted such that the beam strikes the wafer 109 at an oblique angle. In one embodiment, the angle of incidence is 65 degrees but angles greater or less than 65 degrees may be used. The portion of the wafer that is illuminated by the rectangular spot may be imaged with a long working distance, infinity-corrected microscope objective 1129, which is available from Mitutoyo. Additional optical elements occupy the infinity space behind the objective. The light first passes through a mechanically rotatable quarter wave plate 113. The light is then polarization split with a Wollaston prism 114, for example, and each polarization component is imaged with a separate camera. The plane of the Wollaston prism is adjusted at 45 degrees to the plane of incidence. The first mixed component (which includes both P and S components with respect to the plane of incidence) is imaged using a tube lens 1130 onto a linescan camera 1131 available from Hamamatsu. The second mixed component (which includes both P and S components with respect to the plane of incidence) is imaged onto a linescan camera 1133 using a tube lens 1132. It is also possible to use linescan TDI cameras instead of ordinary linescan cameras. In a TDI (time-delay integration) camera, the charge packets are moved across columns of CCD detectors in synchrony with the movement of the object. This synchronization freezes the image on the charge packet wave and has the effect of reducing the required intensity of illumination.

The incident polarization may be adjusted to P, S, or Q, which is at 45 degrees to the plane of incidence (exactly between P and S polarization). With incident polarization set to Q, the instrument is sensitive to measurements of the phase change induced by changes in the resist profile on the wafer surface. The phase shift is measured by taking the difference between the images measured at 1131 and 1133. This gives an output that is proportional to the cosine of the phase difference between the first and second mixed components of the wave. The orientation of the quarter wave plate 113 is adjusted to optimize detection of focus and exposure errors. The specular image may be computed by taking the sum of the images measured at 1131 and 1133. The cameras 1131 and 1133 need to be optically aligned to each other.

The embodiment shown in FIGS. 11-13 allows the simultaneous measurement of the scatter image (darkfield) by placing an imaging channel directly above the rectangular spot on the wafer. A long working distance, infinity-corrected microscope objective 1134 collects the scattered light and a tube lens 1135 images the scattered light onto a linescan CCD or TDI camera 1136. The embodiment of the present invention shown in FIGS. 11-13 measures scatter, specular, and phase images at a single wavelength. It can be modified, however, to operate at multiple wavelengths simultaneously by separating each wavelength into its own channel using dichroic beamsplitters.

The apparatus of the current invention can be operated in different modes and has a number of different adjustments. When it is operated with incident polarization P or S, it will be sensitive to underlying layers or the topmost layer respectively as discussed above. With incident polarization set to Q, the instrument is most sensitive to phase changes caused by the reflecting medium.

In any of the incident polarization modes, the azimuthal angle of the wafer with respect to the incident beam direction is a degree of freedom that can be used to optimize sensitivity to defects of interest. Typically the azimuthal angle is optimized by presenting a sample with known defects of interest, and adjusting the angle to maximize the signal to noise ratio.

On patterned wafers, the defects of interest will be obtained by subtracting the image of one die (or field) from another, either on the same wafer or a different wafer. The difference image (as it is called) will have the majority of the pattern suppressed, and the defect signal should stand out above the noise. The defects can be identified with a thresholding operation. In this context, the noise consists of acquisition noise, alignment errors, and residual signal from the pattern after die-to-die subtraction.

In the phase shift mode, an additional degree of freedom can be found in the angle of the quarter wave plate 113. The quarter wave plate should be rotated to an angle that roughly equalizes the average grey levels of the $S_q$ and $P_q$ signals. Thus, when they are subtracted to obtain the phase image, the pattern will be largely suppressed. This will, in turn, minimize the noise in the difference image. This optimization will thereby maximize the phase signal from such defects as defocus errors. The procedure of optimizing the quarter wave plate angle should be carried out on a wafer with no known phase errors.

The current invention is more sensitive to scanner focus and exposure errors because it directly measures phase changes in the reflected beam. Intensity changes from subtle resist profile variations can be very small. This invention measures changes in the polarization (phase) of the beam and this type of measurement is generally 10 to 20 times more sensitive than intensity measurements.

In alternate embodiments, the laser scanning assemblies shown in FIGS. 1-9 can be modified to provide ellipsometric information as part of the collected data. This can be done either by combining two laser beams with slightly different wavelengths and orthogonal polarizations (e.g., S and P polarization) and splitting the light collected by wavelength and then again by polarization. This yields sufficient information to compute all ellipsometric parameters at a single wavelength. Another alternative is to use a Zeeman-split laser. In this technique, a magnetic field is applied to the laser column of a gas laser. This splits the laser lines into two wavelengths which are closely spaced, but remain coherent. Because the wavelengths are different, a beat frequency between them can be detected with a frequency of Megahertz to hundreds of Megahertz, depending on field strength. The sensor used can then detect the AC and DC components of the returned light, and that data can be processed to provide ellipsometric information. This permits multiple optical components to be removed from the illumination and acquisition paths, but there is a speed limitation given by the beat frequency achievable and the response speed of the sensor and amplifier chain.

Signals collected by the radiation collecting assemblies may be input to a computing system for analysis. As described in U.S. Pat. Nos. 6,665,078, 6,717,671, and 6,757,056, and 6,909,500, incorporated by reference above, the computing system may include an input module to receive signals from the radiation collecting assemblies, a processor, and a memory module. The memory module may include logic instructions which, when executed by the processor, cause the processor to analyze the signals from the radiation collecting assemblies.

Reference in the specification to "one embodiment" or "an embodiment" means that a particular feature, structure, or characteristic described in connection with the embodiment is included in at least an implementation. The appearances of the phrase "in one embodiment" in various places in the specification may or may not be all referring to the same embodiment.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A surface scanning system, comprising:
   a radiation directing assembly to scan a surface using a Cartesian scanning pattern; and
   a radiation collecting assembly that collects radiation reflected from the surface, the radiation collecting assembly comprising:
     a quarter-wave plate; and
     a polarizing beam splitter oriented at an oblique angle relative to the plane of incidence, such that a portion of the radiation reflected from the surface is split into a first mixed component and a second mixed component, each mixed component comprising both P-polarized and S-polarized radiation.

2. The system of claim 1, wherein:
   the radiation directing assembly directs at a constant azimuth angle.

3. The system of claim 1, wherein the radiation directing assembly comprises:
   a radiation source;
   a rotating polygonal mirror that reflects radiation from the radiation source;
   a parabolic mirror to reflect radiation from the rotating polygonal mirror onto the surface.

4. The system of claim 3, wherein the radiation collecting assembly comprises a planar mirror to direct radiation reflected from the surface onto the surface of the parabolic mirror.

5. The system of claim 1, wherein the radiation collecting assembly includes one or more transparent sheets of material that transmit radiation reflected from the surface to a radiation detector.

6. The system of claim 1, further comprising a scan lens that focuses radiation from the radiation source onto the surface.

7. The system of claim 1, wherein the radiation collecting assembly comprises:
   a first radiation collecting assembly to collect radiation specularly reflected from the surface; and
   a second radiation collecting assembly to collect radiation scattered from the surface.

8. The system of claim 7, wherein the second radiation collecting assembly comprises a Fresnel lens.

9. The system of claim 7, further comprising:
   a processor coupled to the first radiation collecting assembly;
   a memory module coupled to the processor and comprising logic instructions which, when executed by the processor, configure the processor to:
     generate a first signal from radiation reflected from the surface; and
     use the first signal to determine a characteristic of the surface.

10. A surface analysis method, comprising:
    scanning a radiation beam across a surface along a Cartesian scanning path;
    collecting radiation reflected from the surface, and radiation scattered from the surface, wherein collecting radiation comprises a splitting a portion of the radiation with a polarizing beam splitter oriented at an oblique angle relative to the plane of incidence, such that a portion of the radiation reflected from the surface is split into a first mixed component and a second mixed component, each mixed component comprising both P-polarized and S-polarized radiation;

and using at least one of the radiation reflected from the surface or the radiation scattered from the surface to detect profile variations in the surface.

11. The method of claim 10, wherein scanning a radiation beam across a surface along a Cartesian scanning path comprises impinging radiation on the surface at a constant azimuth angle.

12. The method of claim 10, wherein scanning a radiation beam across a surface along a Cartesian scanning path comprises traversing the radiation beam across the surface in a serpentine pattern.

13. The method of claim 10, wherein scanning a radiation beam across a surface along a Cartesian scanning path comprises reflecting the radiation beam from a rotating mirror onto a parabolic mirror.

14. The method of claim 10, wherein scanning a radiation beam across a surface along a Cartesian scanning path comprises reflecting radiation from a rotating mirror onto a scan lens.

15. The method of claim 10, wherein collecting radiation reflected from the surface comprises splitting the reflected radiation into a first radiation beam having a first polarization and a second radiation beam having a second polarization.

* * * * *